United States Patent [19]
Giatsintov et al.

[11] Patent Number: 5,858,796
[45] Date of Patent: Jan. 12, 1999

[54] REAGENT AND METHOD FOR SCREENING OF THE FUNCTIONAL CONDITION OF THE BODY

[75] Inventors: Kiril Erastovitch Giatsintov, Mountainside, N.Y.; Serguei V. Khartchenko, 1405 Toronto Dominion Tower, Edmonton Centre, Edmonton, Alberta T5J 0Z2, Canada; Andrea Victorovich Aleksandrov, Moscow, Russian Federation; Nadejda Petrovna Khartchenko, Edmonton, Canada

[73] Assignee: Serguei V. Khartchenko, Edmonton, Canada

[21] Appl. No.: 400,477

[22] Filed: Mar. 8, 1995

Related U.S. Application Data

[63] Continuation of Ser. No. 927,351, Aug. 11, 1992, abandoned.

[51] Int. Cl.$^6$ .......................... G01N 33/66; G01N 33/92
[52] U.S. Cl. ................... 436/95; 436/13; 436/14; 436/16; 436/18; 436/98; 436/108; 436/128; 436/166; 436/178
[58] Field of Search ............... 436/95, 98, 108, 436/128, 178, 13, 14, 16, 18, 166

[56] References Cited

U.S. PATENT DOCUMENTS

| | | | |
|---|---|---|---|
| 3,907,501 | 9/1975 | Sass et al. | 436/128 |
| 3,955,926 | 5/1976 | Fischer | 436/98 |
| 3,986,834 | 10/1976 | Steinbrink, Jr. | 436/108 |
| 4,026,826 | 5/1977 | Yoshida et al. | 260/25 |
| 4,211,845 | 7/1980 | Genshaw et al. | 436/95 |
| 4,391,906 | 7/1983 | Bauer | 436/95 |
| 4,778,630 | 10/1988 | Moreton et al. | 260/410.9 |
| 5,002,566 | 3/1991 | Carpentier et al. | 623/2 |
| 5,071,769 | 12/1991 | Kundu et al. | 436/178 |
| 5,206,334 | 4/1993 | Phelps et al. | 528/204 |

OTHER PUBLICATIONS

The CRC, Handbook of Chemistry and Physics, 63rd ed., 1982–1983, B–108–B–109.
The Sytematic Identification of Organic Compounds, Shriner et al. 1980. 348–349.
Advanced Inorganic Chemistry Comprehensive Text, Cotton et al. 1980. 758–759.
Kharchenko et al. "New Approaches to Diagnosing . . ." *Izv.Akad.Nowk, Ser.Biol.* 1992, No. 4 pp. 575–581.
DeFronza et al. "Insulin Resistance . . ." *Diebetes Care* vol. 14, No. 3, 3–91. pp. 173–194.
Kulig et al. "Cyanide Toxicity" *Environmental Medicine* 7–93 pp. 107–114 vol. 48, #1.
*Ceramic Articles*, Bondia Sanmartin, Onofre, ES–73–420 759, CA82(18):115403u, 1974.
Aldrich Catalog, 23,648–9 Ferric Chloride Hexahydrate, p. 743, 1988–1989.

*Primary Examiner*—Mary E. Ceperley

[57] ABSTRACT

Reagent and method are offered for the screening of the functional condition of the body by the person's saliva. Reagent presents itself as an H2O solution, containing ions of $Fe^{3+}$, chloride ions and multi-atom alcohol .n the concentrations 0.05–3.0M; 0.05–4.0M, and 0.1–5.0M accordingly. Screening is conducted by means of mixing of the persons saliva with the reagent in the following comparison of colour mix with control; during this an orange colour is correlated with the norm; yellow-diabetes SD-1, functional disorders of pancreas; bright-pink and red initial stages of hypertonic disease, diabetes SD-2, pathological influence of smoking; dark-red, developed forms of hypertension, diabetes SD-2, pathogenic-influence of smoking or other toxic substances, leading to the emphasized energetic disorder.

3 Claims, No Drawings

REAGENT AND METHOD FOR SCREENING OF THE FUNCTIONAL CONDITION OF THE BODY

This application is a continuation of application Ser. No. 07/927,351, filed Aug. 11, 1992, now abandoned.

BACKGROUND OF THE INVENTION

1. Field of the Invention

This invention relates to a reagent for mixing with saliva to detect the development of hypertension, diabetes, and adrenocorticotropic disturbances.

2. Description of the Related Art

Various reagents and methods are known for the screening of pathologies resulting from a problem in the body's normal uptake of carbohydrates and lipids (i.e., carbohydrate-lipid exchange violations). Most focus directly upon the function of the pancreas by monitoring the levels of pancreatic products such as insulin within body fluids. Some such products use as their main component powdered carboxylic acid or an indicating reagent which reacts to the changing concentration of ions of hydrogen. As a main acid indicator certain dyes are used, such as methylene yellow and bromocresol green.

Some compositions have been developed for use directly within the mouth cavity. These compositions commonly have a pH of 6.5–7.0 and they contain a 2.5–4.0 percentage of saccharides (by weight) and a 0.0001–0.05 percentage of indicator pH. The point of colour change is in the range of pH 5–7. On the basis of these kinds of compositions, a chewing gum was developed in Japan to screen for certain pathologies. The gum was impregnated with a reagent which was released in the process of chewing to make contact with the subject's saliva. The reagent reacted with hydrogen ions within the subject's saliva to change the colour of the gum, depending upon the pH level of the saliva.

Methods relying on the pH level of saliva have the drawback that this pH level is susceptible to many influences other than underlying pathologies. Therefore, testing this pH level does not guarantee a pathology will be discovered.

Many traditional methods of screening for a pathology, such as monitoring glucose levels in blood, have the drawback that they are invasive. Further, other traditional screening methods, such as urinalysis, are inaccurate.

Accordingly, there is a need for a non-invasive method of monitoring the development of pathologies related to carbohydrate-lipid exchange violations.

SUMMARY OF THE INVENTION

According to the present invention, there is provided a reagent for mixing with saliva in order to screen for and monitor carbohydrate-lipid exchange violations which accompany prediabetes, diabetes, hypertension disease, cyanide toxicity, and adrenocorticotropic disturbances, said reagent comprising a water solution containing 0.05 to 3.0M ions of $Fe^{3+}$, 0.05 to 4.0M of chloride anions and 0.1 to 5.0M of aliphatic alcohol and further comprising 0.03 to 0.05% by weight insoluble substances comprising the following components: calcium, sodium, potassium, nitrate, sulfate, phosphate, copper, zinc, iron(II), lead, and arsenic.

DESCRIPTION OF THE PREFERRED EMBODIMENTS

The reagent of this invention comprises a water solution containing ions of $Fe^{3+}$, chloride anions and aliphatic alcohol in the following concentrations: 0.05 to 3.0M; 0.05 to 4.0M and 0.1 to 5.0M, respectively.

In addition, the reagent comprises 0.03 to 0.05% by weight insoluble substances. These insoluble substances are made up of the following components:

| | |
|---|---|
| calcium | 0.05 to 0.1% |
| sodium | 0.03 to 0.1% |
| potassium | 0.02 to 0.05% |
| nitrate | 0.01 to 0.03% |
| sulfate | 0.01 to 0.03% |
| phosphate | 0.01 to 0.02% |
| copper | 0.01 to 0.02% |
| zinc | 0.01 to 0.02% |
| $Fe^{2+}$ | 0.003 to 0.005% |
| lead | 0.003 to 0.005% |
| arsenic | 0.0003 to 0.0005% |
| filler | 99.6195 to 99.8437% |

In use, 0.03 ml of the reagent is thoroughly mixed with a sample of saliva from the human subject of about 0.3 ml in volume. This may be accomplished by adding the reagent to a resilient capsule, squeezing one end of the capsule, dipping the other end into saliva, releasing the squeezed end such that about 0.3 ml of saliva is introduced into the capsule, then shaking the capsule for about 3.5 seconds. The resultant reaction product will have one of several colours ranging from slightly yellow through orange, pink/red, and dark red.

If the resultant reaction product is orange in colour, the subject is not suffering from any of the pathologies the reagent is sensitive to.

If the resultant reaction product is yellow, is either suffering from a functional disturbance of the pancreas in that there is insufficient insulin production or is suffering from a functional disturbance of the adrenal cortex (such as Cushing's syndrome).

If the resultant reaction product is a saturated pink (light red) or a red colour, the subject is suffering from a dynamic metabolic imbalance due to any of the following: the pathological influence of smoking, the presence of other toxic substances such as cyanide (cyanide toxicity), the vascular disease of hypertension (i.e., increasing arterial and vein pressure), or a pathology resulting from a carbohydrate-lipid exchange violation such as from the early stages of development of type 2 diabetes.

If the resultant reaction product is dark red, the subject is suffering from a substantial (i.e., more serious) dynamic metabolic imbalance due to the pathological influence of smoking or the presence of other toxic substances including the chemical precursors of type 2 diabetes. For the hypertensive patient, the dark red colour indicates the imminent development of hypertonic crisis.

Regarding the mechanism of operation of the reagent of this invention, it is postulated that in pathologies, such as diabetes, which involve a problem in the body's normal uptake of carbohydrates (glucose) and lipids (fatty acids) the body's oxidative processes are disturbed. It is postulated that this disturbance triggers operation of a compensatory mechanism which in part creates minute by-products such as Rodanide as well as certain low molecular metabolites from ketone bodies and acetone. These by-products appear in body fluids, including the saliva and the level of their presence is determined by the extent of the disturbance. While the products of the reaction have not been isolated, evidence suggests that the reagent reacts in varying degrees with the above postulated biological by-products, with the resultant mixture being a coloured product. Thus, certain colours of the reagent indicate a differing degree of metabolic imbalance. The reagent may therefore be used to rapidly, simply, and inexpensively measure those minute dynamic metabolic imbalances which invariably precede the development of hypertension, type I and type II diabetes, and other pathologies resulting from disturbances within the endocrine system which are occasioned by dysfunctions of adrenocorticotropic hormones, adrenaline and insulin.

Table #1 illustrates the specificity and sensitivity of the reagent and method to distinguish patients (previously diagnosed by traditional methods) from healthy persons, inspected in the Center for Endocrinology MNUSSR.

From table #1 it is readily apparent that the offered reagent and method is highly selective for the diseases which involve dynamic metabolic imbalances related to carbohydrate-lipid exchange violations. The reagent, in use, is susceptible to error when dealing with a subject who smokes. Moreover, the reagent and method are incapable of identifying such diseases as cancer of the lungs and stomach cancer (see examples 5 and 6) in which the colouring of the resultant reaction product matches the norm.

Table #2 records the experimental results when the components of the reagent were varied and then used upon saliva samples taken from fifty patients with similar stage hypertonic disease. Aliphatic alcohol, as glycerine (glycerol) or ethylene glycol, was used with varying concentrations of chloride-anions changed by adding the salts KCl and NaCl. Sources of ions of $Fe^{3+}$ were simple non-organic salts such as chloride, sulphate, nitrate and others.

of 0.6 to 3.0M, chloride anions of 0.05 to 4.0M, and alcohol of 0.1 to 5.0M.

The offered reagent and method can be used to reveal minute dynamic metabolic imbalances as precursors to related pathologies in a selective, simple, and rapid manner. As such, the offered reagent and method can be used not only in early diagnosis of such disorders, but also as a means of monitoring the effectiveness of treatment and identifying prophylactic measures. Moreover, in hypertension cases, the reagent and method offer a critical three to four hour period of prior notice of the onset of a hypertonic crisis, allowing for appropriate intervening steps to be taken.

Modifications will be apparent to those skilled in the art and, accordingly, the invention is defined in the claims.

TABLE # 1

| No. 1 | Name of Sickness (by recording verification diagnosis established with help of traditional methods) 2 | Number of observed people 3 | Distribution of people by colour of reagent in percentage | | | |
|---|---|---|---|---|---|---|
| | | | Orange 4 | Yellow 5 | Bright Pink and Red 6 | Dark Red 7 |
| 1 | High Blood pressure Different Studies | | | | | |
| | 1 | 100 | — | — | 30x | 70xx |
| | 2 | 170 | — | — | — | 93–95 |
| | 3 | 50 | — | — | — | 95–97 |
| | 4 | 60 | — | — | — | 95–97 |
| 2 | Diabetes (form of Sugar diabetes-1) | 80 | — | 75 | 25 | |
| 3 | Cushing's Syndrome | 20 | — | 80 | 9 | 11 |
| 4 | Diabetes (form of Sugar diabetes-2) | 120 | — | 15 | — | 85 |
| 5 | Cancer of the Lungs | 50 | 93 | — | — | — |
| 6 | Cancer of the Stomach | 60 | 95 | — | — | — |
| 7 | Healthy People (non-smoking) | 200 | 97 | — | — | — |
| 8 | Healthy People (smokers) | 150 | — | — | 93 | 7 |

For the given data, the reagent comprised a water solution in which there were $Fe^{3+}$ ions, chloride anions and glycerine as a type of aliphatic alcohol in the concentration: 0.8M, 2.4M and 2.0M, respectively; the volume of saliva to reagent was 10 to 1.

x—3 to 4 hours before the rise of blood pressure xx—at a constant high blood pressure

TABLE # 2

| # 1 | MULTI-ATOM ALCOHOL 2 | MOL CONCENTRATION | | | DIVISION OF COLOUR | | | |
|---|---|---|---|---|---|---|---|---|
| | | ION $Fe^{3+}$ 3 | CLORIDE ANION 4 | MULTI-ATOM ALCOHOL 5 | ORANGE 6 | YELLOW 7 | PINK OR RED 8 | DARK RED 9 |
| 1 | Glycerine- | 0.8 | 2.4 | 2.0 | — | — | — | 95–97 |
| 2 | Ethyleneglycol | 2.1 | 3.5 | 5.0 | — | — | 5–7 | 93–95 |
| 3 | Glycerine | 0.05 | 2.0 | 3.0 | — | — | 7–10 | 90–93 |
| 4 | Glycerine | 3.0 | 3.5 | 0.1 | — | — | 4–6 | 94–96 |
| 5 | Glycerine | 0.1 | 0.05 | 2.0 | — | — | 9–11 | 89–91 |
| 6 | Glycerine | 2.5 | 4.0 | 4.0 | — | — | 8–10 | 90–92 |

Table #2 illustrates that for diagnostic purposes, the optimal reagent component mixture comprises ions of $Fe^{3+}$ The embodiments of the invention in which an exclusive property or privilege is claimed are defined as follows:

1. A method for screening for carbohydrate-lipid metabolism violations in an individual which accompany prediabetes, diabetes, hypertension disease, and adrenocorticotropic disturbances, comprising the steps of:
   1) mixing saliva of said individual with an effective amount of a reagent comprising a water solution containing:
      a. 0.05 to 3.0M $Fe^{3+}$ resulting from addition of a $Fe^{3+}$ salt, said salt including the following substances in the stipulated concentration ranges, expressed by weight:

| | |
|---|---|
| calcium | 0.05 to 0.1% |
| sodium | 0.03 to 0.1% |
| potassium | 0.02 to 0.05% |
| nitrate | 0.01 to 0.03% |
| sulfate | 0.01 to 0.03% |
| phosphate | 0.01 to 0.02% |
| copper | 0.01 to 0.02% |
| zinc | 0.01 to 0.02% |
| iron (II) | 0.003 to 0.005% |
| lead | 0.003 to 0.005% |
| arsenic | 0.0003 to 0.0005% | b. 0.05 to 4.0M chloride anions; and
   c. 0.1 to 5.0M aliphatic alcohol;
   ii) determining the likely presence of one of said carbohydrate-lipid metabolism violations based on the resultant colour of the mixture of reagent and saliva wherein said reagent turns orange when mixed with the saliva of a healthy individual, turns light red when mixed with the saliva of an individual who is suffering from hypertension, or prediabetes, and turns dark red when mixed with the saliva of an individual who is suffering from diabetes or who may be imminently developing hypertonic crisis or a severe insulin disorder or an adrenocorticotropic disorder.

2. The method of claim 1 wherein said saliva is mixed with said reagent in a ratio of 10 parts saliva to 1 part reagent.

3. A method for monitoring for carbohydrate-lipid metabolism violations in an individual which accompany prediabetes, diabetes, hypertension disease, and adrenocorticotropic disturbances, comprising the steps of:
   i) mixing saliva of said individual at different times over a course of a period with an effective amount of reagent comprising a water solution containing:
      a. 0.05 to 3.0M $Fe^{3+}$ resulting from addition of a $Fe^{3+}$ salt, said salt including the following substances in the stipulated concentration range, expressed by weight:

| | |
|---|---|
| calcium | 0.05 to 0.1% |
| sodium | 0.03 to 0.1% |
| potassium | 0.02 to 0.05% |
| nitrate | 0.01 to 0.03% |
| sulfate | 0.01 to 0.03% |
| phosphate | 0.01 to 0.02% |
| copper | 0.01 to 0.02% |
| zinc | 0.01 to 0.02% |
| iron (II) | 0.003 to 0.005% |
| lead | 0.003 to 0.005% |
| arsenic | 0.0003 to 0.0005% | b. 0.05 to 4.0M chloride anions; and
   c. 0.1 to 5.0M aliphatic alcohol.
   ii) determining the likely presence of one of said carbohydrate-lipid metabolism violations based on the resultant colour of the mixture of reagent and saliva wherein said reagent turns orange when mixed with the saliva of a healthy individual, turns light red when mixed with the saliva of an individual who is suffering from hypertension, or prediabetes, and turns dark red when mixed with the saliva of an individual who is suffering from diabetes or who may be imminently developing hypertonic crisis or a severe insulin disorder or an adrenocorticotropic disorder.

* * * * *